(12) United States Patent
Inbasekaran et al.

(10) Patent No.: US 7,893,160 B2
(45) Date of Patent: Feb. 22, 2011

(54) CROSSLINKABLE SUBSTITUTED FLUORENE COMPOUNDS AND CONJUGATED OLIGOMERS OR POLYMERS BASED THEREON

(75) Inventors: Michael Inbasekaran, Palatine, IL (US); Wanglin Yu, Midland, MI (US)

(73) Assignee: Sumitomo Chemical Company, Limited, Tokyo (JP)

( * ) Notice: Subject to any disclaimer, the term of this patent is extended or adjusted under 35 U.S.C. 154(b) by 1072 days.

(21) Appl. No.: 10/579,531

(22) PCT Filed: Oct. 25, 2004

(86) PCT No.: PCT/US2004/036076

§ 371 (c)(1),
(2), (4) Date: Sep. 1, 2006

(87) PCT Pub. No.: WO2005/049689

PCT Pub. Date: Jun. 2, 2005

(65) Prior Publication Data

US 2007/0102695 A1    May 10, 2007

Related U.S. Application Data

(60) Provisional application No. 60/520,597, filed on Nov. 17, 2003.

(51) Int. Cl.
*C08F 8/00* (2006.01)
*C08G 75/00* (2006.01)
*C07D 491/02* (2006.01)
*C07D 498/02* (2006.01)
*H01L 51/00* (2006.01)

(52) U.S. Cl. ................ 525/191; 528/379; 528/396; 528/503; 548/126; 548/151; 548/218; 564/427; 428/411.1; 257/40; 257/E51.02

(58) Field of Classification Search ........... 257/40, 257/E51.02; 528/379, 396, 503; 525/191; 548/126, 151, 218; 564/427; 428/411.1
See application file for complete search history.

(56) References Cited

U.S. PATENT DOCUMENTS

| | | | |
|---|---|---|---|
| 4,983,482 A | 1/1991 | Ong et al. | |
| 5,728,801 A | 3/1998 | Wu et al. | |
| 5,777,070 A | 7/1998 | Inbasekaran et al. | |
| 5,929,194 A | 7/1999 | Woo et al. | |
| 5,962,631 A | 10/1999 | Woo et al. | |
| 6,169,163 B1 | 1/2001 | Woo et al. | |
| 6,255,447 B1 | 7/2001 | Woo et al. | |
| 6,255,449 B1 | 7/2001 | Woo et al. | |
| 6,309,763 B1 | 10/2001 | Woo et al. | |
| 6,362,310 B1 | 3/2002 | Woo et al. | |
| 6,512,083 B1 | 1/2003 | Woo et al. | |
| 6,514,632 B1 | 2/2003 | Woo et al. | |
| 6,559,256 B2 | 5/2003 | Holmes et al. | |
| 6,605,373 B2 | 8/2003 | Woo et al. | |
| 2004/0054152 A1 | 3/2004 | Meerholz et al. | |

FOREIGN PATENT DOCUMENTS

| | | |
|---|---|---|
| CN | 1263542 A | 8/2000 |
| WO | 9954385 A | 10/1999 |
| WO | WO 2004/072123 A2 | 8/2004 |

OTHER PUBLICATIONS

G. Klarner, J.I. Lee, V.Y. Lee, E. Chan, J.P. Chen, A. Nelso, D. Markiewicz, R. Siemens, J.C. Scott, and R.D. Miller Cross-linkable Polymers Based on Dialkylfluorenes Chem. Matter. 1999, 11, 1800-1805.

Thomas Braig et al., "Crosslinkable hole-transporting polymers by palladium-catalyzed C-N-coupling reaction", Macromol. Rapid Commun., 1999, pp. 583-589, vol. 21, No. 9, Wiley-VCH Verlag GmbH, D-69451 Weinheim.

Michael S. Bayer et al., "Crosslinkable hole-transport materials for preparation of multilayer organic light emitting devices by spin-coating", Macromol. Rapid Commun., 1999, pp. 224-228, vol. 20, No. 4, Wiley-VCH Verlag GmbH, D-69451 Weinheim.

Norio Miyaura et al., "Palladium-Catalyzed Cross-Coupling Reactions of Organoboron Compounds", Chemical Review, 1995, pp. 2457-2483, vol. 95, American Chemical Society.

I. Colon et al., "High Molecular Weight Aromatic Polymers by Nickel Coupling of Aryl Polychlorides", Journal of Polymer Science: Part A: Polymer Chemistry Edition, 1990, pp. 367-383, vol. 28, John Wiley & Sons, Inc.

Ismael Colon et al., "Coupling of Aryl Chlorides by Nickel and Reducing Metals", Journal of Organic Chemistry, 1986, pp. 2627-2637, vol. 51, American Chemical Society.

Masahiko Iyoda et al., "Homocoupling of Aryl Halides Using Nickel(II) Complex and Zinc in the Presence of $Et_4NI$. An Efficient Method for the Synthesis of Biaryls and Bipyridines", Bulletin of the Chemical Society of Japan, 1990, pp. 80-87, vol. 63, No. 1, The Chemical Society of Japan.

Takakazu Yamamoto, "Electrically Conducting and Thermally Stable Π-Conjugated Poly(Arylene)S Prepared by Organometallic Processes", Progress in Polymer Science, 1992, pp. 1153-1205, vol. 17, Pergamon Press Ltd.

Wayne R. Sorenson et al., "Preparative Methods of Polymer Chemistry", Second Edition, 1968, pp. 1-504, Interscience Publishers.

P.E. Burrows et al., "Metal ion dependent luminescence effects in metal tris-quinolate organic heterjunction light emitting devices", Applied Physics Letters, 1994, pp. 2718-2720, vol. 64, No. 20, American Institute of Physics.

Yuji Hamada et al., "High Luminance in Organic Electroluminescent Devices with Bis(10-hydroxybenzo[h]quinolinato)beryllium as an Emitter", Chemistry Letters, 1993, pp. 905-906, The Chemical Society of Japan.

Yuji Hamada et al., "Organic Electroluminescent Devices with Bright Blue Emission", Optoelectronics—Devices and Technologies, 1992, pp. 83-93, vol. 7, No. 1, MITA Press.

(Continued)

*Primary Examiner* — Duc Truong
(74) *Attorney, Agent, or Firm* — Sughrue Mion, PLLC

(57) ABSTRACT

Crosslinkable substituted fluorene compounds; oligomers and polymers prepared from such crosslinkable compounds; films and coatings; and multilayer electronic devices comprising such films are disclosed.

9 Claims, No Drawings

OTHER PUBLICATIONS

Junji Kido et al., "Blue Electroluminescent 1,2,4-Triazole Derivative", Chemistry Letters, 1996, pp. 47-48.

Masayoshi Yoshida et al., "Three-layered multicolor organic electroluminescent device", Applied Physics Letters, 1996, pp. 734-736, vol. 69, No. 6, American Institute of Physics.

Xiao-Chang Li et al., "Synthesis and Optoelectronic Properties of Aromatic Oxadiazole Polymers", Journal of Chemical Society, Chemical Commun., 1995, pp. 2211-2212.

Y. Yang et al., "Electron injection polymer for polymer light-emitting diodes", Journal of Applied Physics, 1995, pp. 4807-4809, vol. 77, No. 9, American Institute of Physics.

Marko Strukelj et al., "Design and Application of Electron-Transporting Organic Materials", Science, 1995, pp. 1969-1972, vol. 267.

Takakazu Yamamoto et al., "Polymer Light-Emitting Diodes with Single- and Double-Layer Structures Using Poly(2,3-diphenylquinoxaline-5,8-diyl)", Japan Journal of Applied Physics, 1994, pp. L250-L253, vol. 33, Part 2, No. 2B.

D. O'Brien et al., "Electroluminescence applications of a poly(phenyl quinoxaline)", Synthetic Metals, 1996, pp. 105-108, vol. 76, Elsevier Science S.A.

M.S. Weaver et al., "Recent progress in polymers for electroluminescence: microcavity devices and electron transport polymers", Thin Solid Films, 1996, pp. 39-47, vol. 273, Elsevier Science S.A.

CROSSLINKABLE SUBSTITUTED FLUORENE COMPOUNDS AND CONJUGATED OLIGOMERS OR POLYMERS BASED THEREON

CROSS-REFERENCE STATEMENT

This application claims the benefit of U.S. Provisional Application No. 60/520,597, filed Nov. 17, 2003.

BACKGROUND OF THE INVENTION

This invention relates to novel crosslinkable fluorene compounds and methods for their preparation. The invention further relates to oligomers and polymers of such compounds, including crosslinked derivatives thereof, as well as films and coatings prepared from such compounds, oligomers or polymers, processes for preparing such films and coatings, and electronic devices, especially electroluminescent devices, comprised of one or more layers of such polymer films.

U.S. Pat. Nos. 6,605,373, 6,362,310, 6,255,449, 6,255,447, 6,169,163, 5,962,631 and related patents disclosed certain crosslinkable substituted fluorene compounds and oligomers and polymers therefrom. *Macromolecular Rapid Communication* 21, 583-589 (2000) described the synthesis of arylamine containing crosslinkable hole transport materials containing a crosslinkable oxetane group. *Macromolecular Rapid Communication* 20, 224-228 (1999) described the synthesis of triarylamine small molecules with crosslinkable oxetane groups that can be spin-coated and crosslinked as films. The foregoing references, to the extent crosslinked polymers are disclosed, lack a conjugated polymer backbone, and have only restricted charge transport ability.

In WO 2004/072123 fluorendiyl containing compounds are disclosed for use in organic light-emitting displays. Related compounds are also disclosed in U.S. Pat. No. 6,559,256 and USA 2004/0054152, published Mar. 18, 2004.

Recent advances in display technology have resulted in improved compounds and fabrication techniques for electroluminescent devices such as light-emitting diodes (LED's). High luminance materials are now available for a large portion of the visible light spectrum, including blue light emitting compounds. Recently it has been discovered that improved lifetimes and efficiencies of the active or light emitting layer of a multilayer LED can be obtained by incorporation of a charge transport layer into a multilayer LED between the active or light emitting layer and the anode. Such layers may also be referred to as a hole injection and/or hole transport layer where the purpose is to improve hole injection into the light emitting layer and to provide a buffer layer between the anode and the light emitting layer. In other applications, such an inter-layer between the hole transport layer and light emitting layer has been shown to provide improved device efficiency and lifetime.

The present invention is directed to novel compounds for use in hole transport layers and interlayers of a multilayer LED, as well as in other electronic devices such as field effect transistors (FET's), photovoltaic cells, and even for integrated circuits or printed circuit boards.

SUMMARY OF THE INVENTION

In one aspect, this invention is a cross-linkable compound containing one or more fluorendiyl groups of the formula:

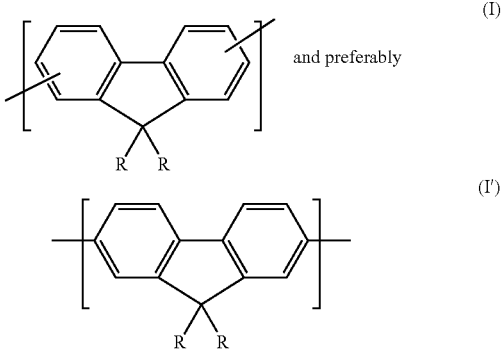

and preferably where R, independently each occurrence, is an inert substituent, a monovalent crosslink forming group, X, or a polyvalent crosslink forming group, X', with the proviso that in at least one repeat unit per molecule, at least one R is X or X'.

Due to the pendant nature of the crosslinkable groups, X and X', the compounds of the present invention are capable of forming oligomers and polymers containing relatively large amounts of conjugated unsaturation, thereby resulting in improved charge transport properties. Oligomers and polymers, including copolymers, resulting from crosslinking compositions comprising the foregoing compounds advantageously are characterized by reduced ionization potential and improved conductivity. Moreover, the compounds are capable of forming crosslinked, solvent resistant films that are well suited for use as interlayers or light emitting layers in electroluminescent devices.

Accordingly, in a second aspect, this invention is a crosslinkable composition comprising oligomers or polymers having repeat units of the empirical formula:

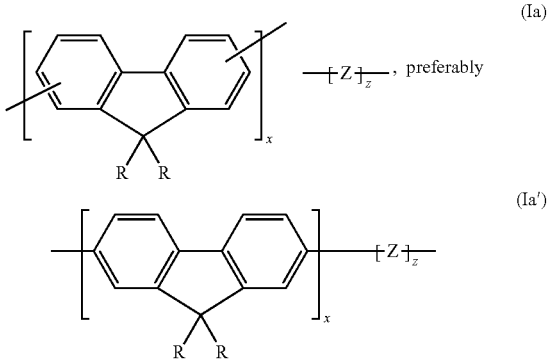

where R, independently each occurrence, is an inert substituent, a monovalent crosslink forming group, X, or a polyvalent crosslink forming group, X', with the proviso that in at least one repeat unit per molecule, at least one R is X or X';

Z is a divalent remnant of a copolymerizable comonomer or a monovalent chain terminating group; and x is a number from 1 to 10,000 and z is a number from 0 to 10,000 signifying the average number of repeat units in the composition.

In a third aspect, this invention is a process for preparing oligomers or polymers, including copolymers, of formula Ia or Ia', which process comprises heating one or more compounds comprising at least one unit of formula I or a composition comprising the same, such as a mixture thereof with one or more addition polymerizable comonomers able to form polymeric component Z, optionally in the presence of any other noninterfering compound, under reaction conditions sufficient to form an oligomer or polymer of Formula Ia or Ia'.

In a fourth aspect, this invention comprises a cross-linked polymer having repeat units corresponding to formula;

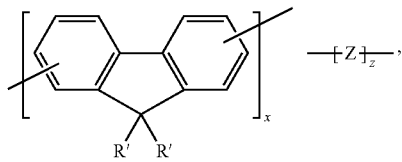

(Ib)

and preferably corresponding to the formula:

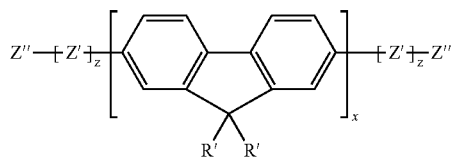

wherein

R' independently each occurrence is R or a crosslinked derivative of X or X' with the proviso, that in at least one occurrence, R' is a crosslinked derivative of X or X', and X, X', R, Z, x and z are as previously defined.

In a fifth aspect, this invention is a film comprising one or more of the oligomers or polymers of the second or fourth embodiment of this invention or preparable according to the third embodiment of this invention.

In a sixth aspect, this invention is an electronic device comprising one or more layers of polymer films, at least one of which comprises a film according to the fifth aspect of the invention.

The foregoing compounds, oligomers and polymers have been discovered to possess especially efficient hole injecting/transporting or electron blocking properties when used to form interlayers in electronic devices, and advantageously are characterized by reduced ionization potential and improved conductivity. Moreover, the compounds are capable of forming crosslinked, solvent resistant films that are well suited for use as such interlayers in electronic devices such as LEDs.

DETAILED DESCRIPTION OF THE INVENTION

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless stated otherwise or apparent from the context, refers to the listed members individually as well as in any combination.

As used herein the term "aromatic" refers to a polyatomic, cyclic, ring system containing $(4\delta+2)$ π-electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings.

"B-Staged" refers to the oligomeric mixture or low molecular weight polymeric mixture resulting from partial polymerization of a monomer. Unreacted monomer may be included in the mixture.

"Conjugation" refers to full or partial overlap of adjacent π-, p- or d-orbital electrons associated with atoms in the polymer chain of interest. Conjugation is presumed to exist between two entities containing atoms possessing delocalized charges, such as double or triple bonds, which are joined to one another by a covalent bond or by a —S—, —O—, —NR—, —PR—, —BR—, or —SiR$_2$— group.

"Crosslinkable" means a functional group that is capable of being irreversibly cured or polymerized, thereby forming a material that cannot be reshaped or reformed. Crosslinking may be assisted by heat or by UV, microwave, x-ray, or e-beam irradiation. The term is often used interchangeably with "thermosettable" when the crosslinking is done thermally.

"Hydrocarbyl" refers to a univalent moiety containing only carbon and hydrogen atoms.

"Hydrocarbylene" refers to a divalent moiety containing only carbon and hydrogen atoms.

"Inert" means a substituent group or compound which does not interfere with any desired preparation or synthesis herein, or with any subsequent reaction, coupling, or polymerization of the invented compositions. Suitable inert substituents include hydrogen, $C_{1-20}$ hydrocarbyl and tri($C_{1-20}$hydrocarbyl)silyl groups.

"Leaving group" means a substituent that is readily displaced or eliminated from the molecule under coupling conditions. Examples of suitable leaving groups include halo, cyano, triflate, azide, —B(OR)$_2$, and

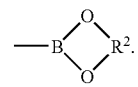

wherein $R^1$, independently in each occurrence, is an inert substituent, preferably hydrogen or a $C_{1-10}$ alkyl group, and $R^2$, independently each occurrence, is a $C_{2-10}$ alkylene group. A preferred leaving group is bromo.

Examples of monofunctional crosslinkable X groups are moieties containing a double bond, a triple bond, a precursor capable of in situ formation of a double bond, or a heterocyclic, addition polymerizable group. Preferred crosslinkable X groups include substituted $C_{6-12}$ arylene or aralkylene groups containing one or more substituents selected from the group consisting of benzocyclobutane, azide, oxirane, di(hydrocarbyl)amino, cyanate ester, hydroxy, glycidyl ether, $C_{1-10}$ alkylacrylate, $C_{1-10}$ alkylmethacrylate, alkenyl, alkenyloxy, alkynyl, maleimide, nadimide, tri($C_{1-4}$)-alkylsiloxy, tri($C_{1-4}$) alkylsilyl, and halogenated derivatives thereof. Most preferred crosslinkable X groups are vinylbenzyl, p-ethenylphenyl, perfluoroethenyl, perfluroethenyloxy, benzo-3,4-cyclobutan-1-yl and p-(benzo-3,4-cyclobutan-1-yl)phenyl.

Specific examples of suitable crosslinkable X groups include: —$(R^4)_p$—$CR^3$=$CR^3{}_2$, —$(R^4)_p$—C≡$CR^3$, —$(R^4)_p$—O($R^4$)$_p$ $CR^3$=$CR^3{}_2$, —$(R^4)_p$—O($R^4$)$_p$ C≡$CR^3$, —$(R^4)_p$—C(O)($R^4$)$_p$ $CR^3$=$CR^3{}_2$, —$(R^4)_p$—C(O)($R^4$)$_p$ C≡$CR^3$, —$(R^4)_p$—OC(O)($R^4$)$_p$ $CR^3$=$CR^3{}_2$, —$(R^4)_p$—OC(O)($R^4$)$_p$ C≡$CR^3$, —$(R^4)_p$—COO($R^4$)$_p$ $CR^3$=$CR^3{}_2$, —$(R^4)_p$—COO($R^4$)$_p$C≡$CR^3$, —$(R^4)_p$—O(CO)O($R^4$)$_p$ $CR^3$=$CR^3{}_2$, —$(R^4)_p$—O(CO)O($R^4$)$_p$—C≡$CR^3$, $NR^3{}_2$,

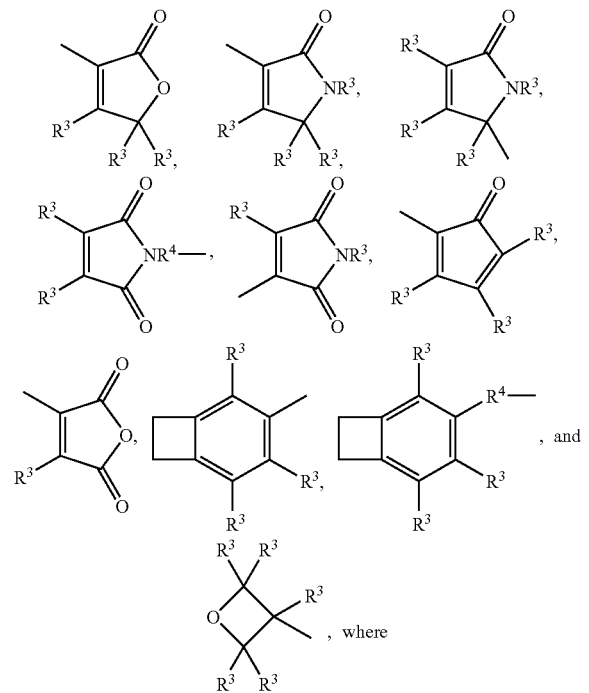

, and

, where $R^3$ is hydrogen, halogen, $C_{1-20}$ hydrocarbyl, $C_{1-20}$ halohydrocarbyl, or $C_{1-20}$ halocarbyl;

$R^4$ is $C_{1-20}$ hydrocarbylene, $C_{1-20}$ halohydrocarbylene, or $C_{1-20}$ halocarbylene, preferably arylene, most preferably p-phenylene; and p is 0 or 1.

In like vein, polyfunctional X' groups are substituents comprising two or more of the foregoing crosslinkable X functional groups. It will be understood by the skilled artisan, that crosslinking of an X functional group involves a reaction between two or more X groups in two or more different compounds, oligomers or polymers, or a reaction of an X group with a separately added polymerizable comonomer, thereby joining said molecules into a single chemical entity.

In one preferred embodiment of the invention, X groups comprise an aromatic moiety, preferably a moiety of the formula ArX", wherein Ar is a divalent aromatic group of up to 20 atoms not counting hydrogen and X" is a crosslinkable group having at least one of the crosslink forming atoms thereof covalently bound to an atom of Ar bearing delocalized electronic charge. That is, the X" group is directly attached to an aromatic group comprising Ar. Especially suited X" groups in this embodiment include p-ethenylphenyl, p-vinylbenzyl or benzo-3,4-cyclobutan-1-yl groups, and inertly substituted derivatives thereof. In yet another preferred embodiment, the X groups are self-crosslinkable, meaning that no initiator, such as an acid, base or peroxide compound, is needed to initiate crosslinking involving said X group, it being understood that copolymerizable comonomers, especially addition polymerizable comonomers such as ethylenically unsaturated compounds, may additionally be present. In this embodiment, the absence of an acid, base or peroxide initiator, reduces corrosion of the cathode or other components of the resulting electronic device and eliminates problems due to proton migration within the interlayer.

Suitable inert, non-crosslinkable R groups include $C_{1-20}$ hydrocarbyl and halogenated $C_{1-20}$ hydrocarbyl groups, especially aryl and alkaryl groups. Preferred non-crosslinkable R groups include phenyl and $C_{1-10}$ alkylphenyl, especially p-n-butylphenyl.

Suitable Ar groups include phenylene, biphenylene, naphthalenediyl, anthracenediyl, stilbenediyl, and fluorenediyl groups, inertly substituted derivatives thereof, and combinations of the foregoing groups.

Preferred fluorenediyl containing compounds according to the invention correspond to the formula:

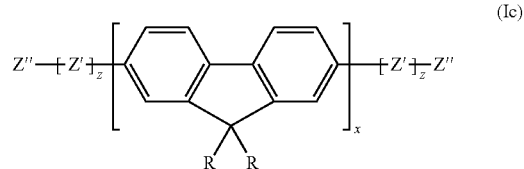

(Ic)

where R, x and z are as previously defined;

Z" is a monovalent chain terminating group; and

Z' is a divalent, repeat unit comprising conjugated unsaturation, more preferably including one or more arylene groups, such as phenylene-, thiophenediyl-, furandiyl-, or pyrroldiyl-groups, or inertly substituted derivatives thereof.

Examples of suitable Z' groups include:

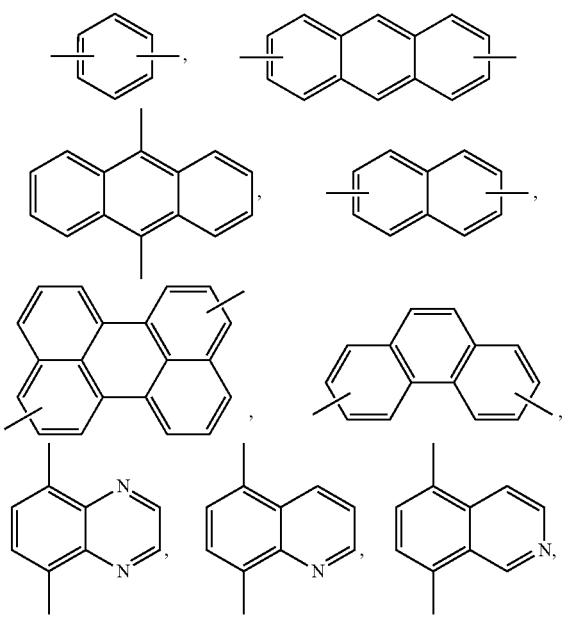

-continued
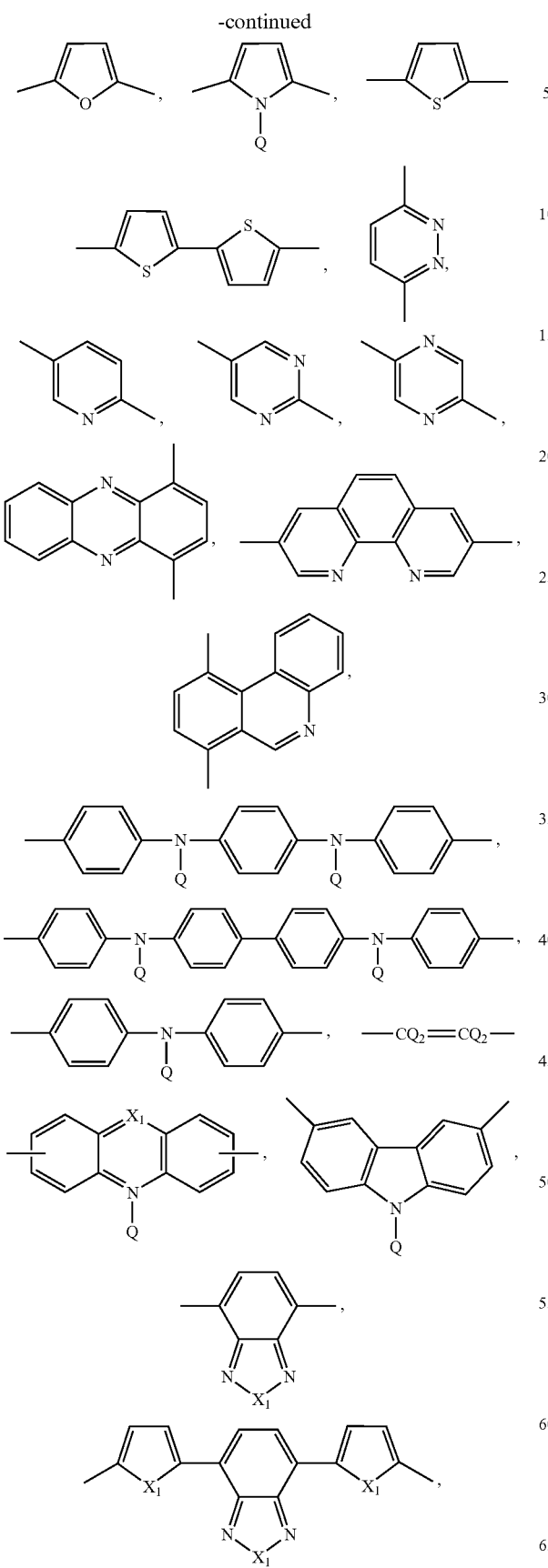
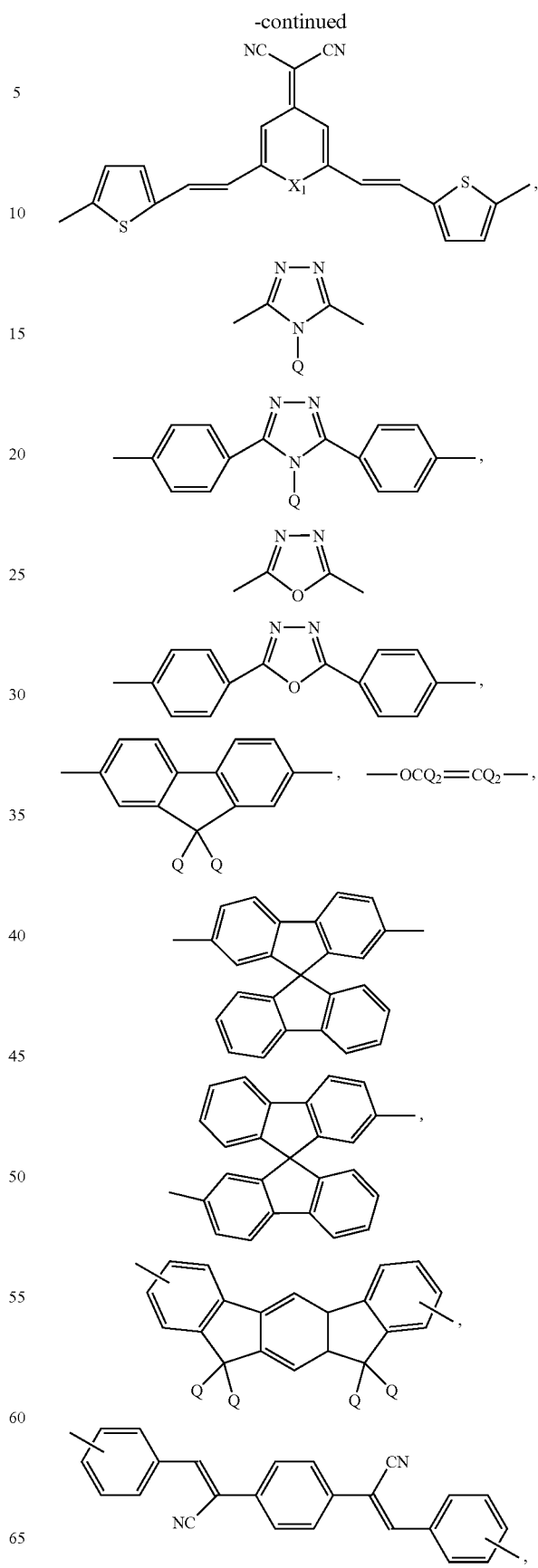

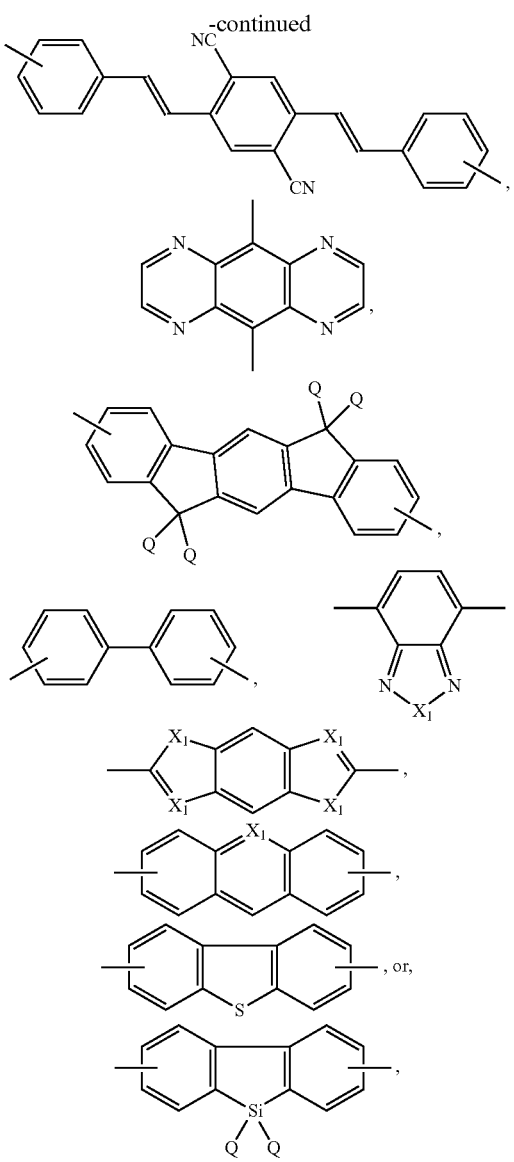

and inertly substituted derivatives thereof;

where $X_1$ is O or S, and Q is halo, alkyl, aralkyl, haloalkyl, cycloalkyl, aryl (including heteroaryl and polycycloaryl), or combinations thereof, said Q having of up to 40 atoms not counting hydrogen.

Suitable substituents on the foregoing structures, including any Q groups thereon, are independently each occurrence selected from the group consisting of $C_{1-20}$ hydrocarbyl, $C_{1-20}$ hydrocarbyloxy, $C_{1-20}$ hydrocarbylsulfido, $C_{1-20}$ hydrocarbylcarboxyl, $C_{1-20}$ hydrocarbylcarbonyloxy, tri($C_{1-20}$)hydrocarbylsilyl, and cyano.

Preferred Q groups include alkyl, aralkyl, haloalkyl, or cycloalkyl of up to 20 atoms not counting hydrogen; and inertly substituted or unsubstituted aryl groups of up to 40 atoms not counting hydrogen. Highly desired Q groups include phenyl, alkylated phenyl, 2-fluorenyl, anthracenyl, phenantherenyl, pyrrolyl, pyridinyl, isoquinolinyl, quinolinyl, triazinyl, triazolyl, benzotriazolyl, and phenanthridinyl.

More preferred Z' groups are selected from the units of the formula:

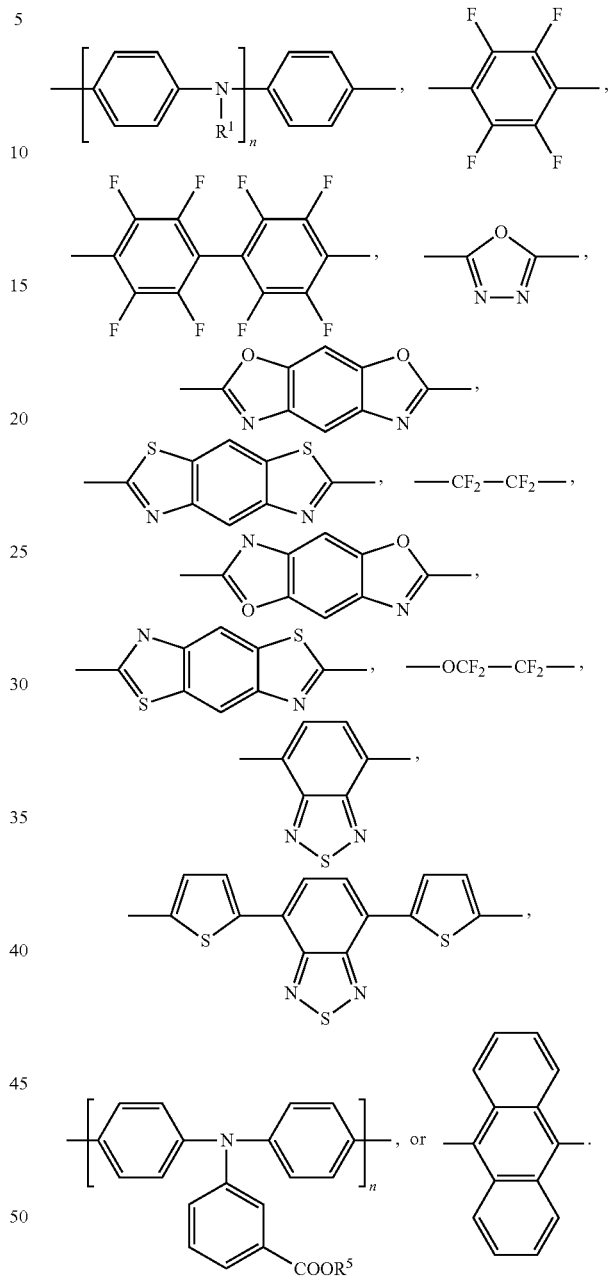

where $R^1$, independently each occurrence, is an inert substituent, X or X', $R^5$ is $C_{1-10}$ alkyl, aryl or aralkyl; and n is 1 or 2.

Preferred substituents, $R^1$, include $C_{1-40}$ hydrocarbyl groups or $C_{1-40}$ hydrocarbyl groups containing one or more S, N, O, P, or Si heteroatoms, and the foregoing $C_{1-40}$ hydrocarbyl or $C_{1-40}$ heteroatom containing groups substituted by a crosslinkable X group. In a more preferred embodiment, $R^1$ is a $C_{1-10}$ alkyl group.

The compounds of the invention, especially the cured oligomers and polymers preferably are highly conjugated, if not completely conjugated, along the backbone defined by crosslinkable fluorendiyl groups and Z' groups. The most highly preferred compounds are those containing 2,7-substitution of the fluorendiyl moiety, although 1,5-, 1,6-, 1,7-, 1,8-, 2,5-, 2,6-, 2,8-, 3,5-, 3,6-, 3,7-, 3,8-, 4,5-, 4,6-, 4,7-, or 4,8-substitution is possible as well.

In a further preferred embodiment, the backbone comprises difunctional derivatives of both fluorene and triarylamine Z' groups. That is, the compounds also contain crosslinking groups corresponding to the formula:

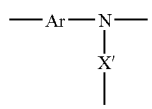

Highly preferred embodiments of the foregoing compounds are those wherein Ar each occurrence is 1,4-phenylene, 9,9-di($C_{1-20}$alkyl)fluoren-2,7-diyl, or a combination thereof; X' is the crosslinked remnant of a 3,4-Benzocyclobutan-1-yl, ethenyl, vinylacrylate, p-vinylbenzyl, or p-ethenylphenyl group; and Z' is hydrogen or bromine. Further preferred amongst these compounds are those wherein Ar each occurrence is phenylene; each X group is 3,4-Benzocyclobutan-1-yl or p-vinylbenzyl; and Z" each occurrence is hydrogen or bromine.

Preferred examples of the compounds of formula Ia according to the present invention are those having the following structure:

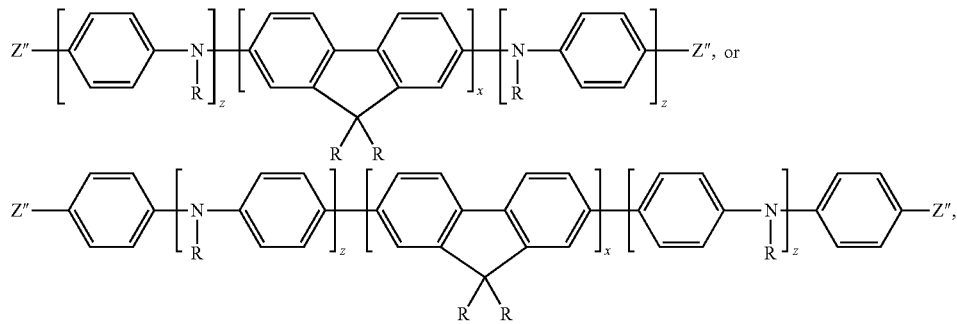

where R, Z", x and z are as previously defined. Both random and block copolymers are included in the foregoing formula. Highly preferably for the monomers of the invention, x is 1 and z, each occurrence, is 1.

Oligomers and polymers according to the present invention are readily prepared using conventional synthetic techniques to cause loss or polymerization of the leaving group, Z", and formation of covalent bonds between monomer units. Suitable techniques include the well known Buchwald or half-Buchwald reaction, Suzuki coupling reactions, or similar techniques.

The oligomers and polymers are highly suited for use in the preparation of both hole transport films and interlayer films in electroluminescent devices.

Crosslinking of Monomers

The compounds of formula Ia or Ib of the invention are readily crosslinked by heating a composition comprising such compound at an elevated temperature for a time sufficient to result in addition polymerization or other crosslinking reaction of at least some X or X' functionality. In one embodiment the compounds are copolymerized with one or more copolymerizable monomers capable of forming divalent crosslinking moieties. Preferred copolymerizable compounds for use herein correspond to the formulas II or III:

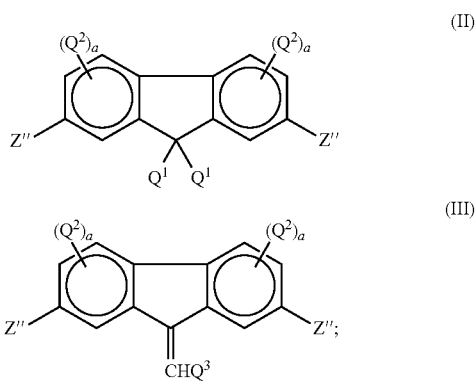

wherein $Q^1$ is independently in each occurrence $C_{1-20}$ hydrocarbyl or $C_{1-20}$ hydrocarbyl containing one or more S, N, O, P or Si atoms, $C_{4-16}$ hydrocarbyl carbonyloxy, $C_{4-16}$ aryl(trialkylsiloxy) or both $Q^1$ may form with the 9-Carbon on the fluorene ring a $C_{5-20}$ ring structure or a $C_{4-20}$ ring structure containing one or more of S, N or O;

$Q^2$ is independently in each occurrence $C_{1-20}$ hydrocarbyl, $C_{1-20}$ hydrocarbyloxy, $C_{1-20}$ thioether, $C_{1-20}$ hydrocarbylcarbonyloxy or cyano;

$Q^3$ is independently in each occurrence $C_{1-20}$ hydrocarbyl or $C_{1-20}$ hydrocarbyl substituted with di($C_{1-20}$ alkyl)amino, $C_{1-20}$ hydrocarbyloxy or $C_{1-20}$ hydrocarbyl or tri($C_{1-10}$ alkyl) siloxy;

a is independently in each occurrence 0 or 1; and

Z" is a leaving group, especially bromo.

In a preferred embodiment, the oligomers and polymers of the invention comprise from 1 to 99 percent, more preferably from 2 to 50 percent, and most preferably from 2 to 10 percent of repeat units of formula Ia or Ib and 99 to 1 percent, more preferably 98 to 50 percent, most preferably 98 to 90 percent of repeat units of the formula:

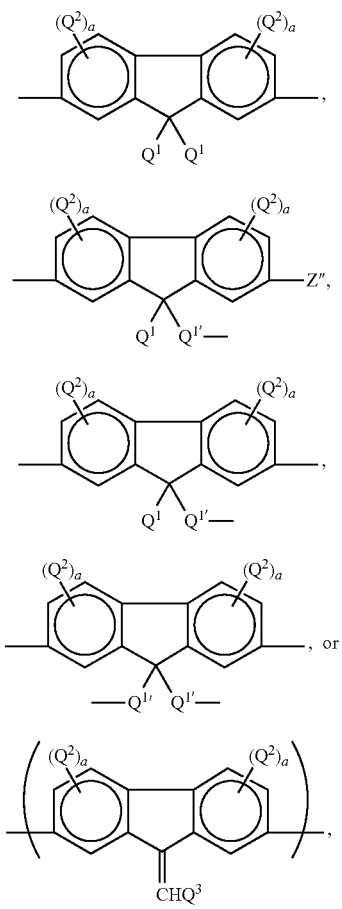

wherein $Q^{1'}$, is a covalent bond or the divalent remnant of $Q^1$.

The monomers and oligomers or b-staged derivatives of the invention are readily soluble in common organic solvents. They are also processable into thin films or coatings by conventional techniques, particularly solution spin coating or ink-jet printing, with or without the use of a solvent.

The oligomers or polymers of this invention preferably have a weight average molecular weight of 1000 Daltons or greater, more preferably 5000 Daltons or greater, even more preferably 10,000 Daltons or greater, highly preferably 15,000 Daltons or greater and most preferably 20,000 Daltons or greater; preferably 1,000,000 Daltons or less, more preferably 750,000 Daltons or less and most preferably 400,000 Daltons or less. Molecular weights are determined by use of gel permeation chromatography using polystyrene standards. The degree of polymerization of the polymers of the invention as measured by the number of repeat units therein is preferably at least 2, more preferably at least 3. Preferably, the oligomers or polymers demonstrate a polydispersity (Mw/Mn) of 5.0 or less, more preferably 3.0 or less, and most preferably 2.0 or less.

Processes for Preparing Oligomers or Polymers

The compounds, oligomers and polymers of the invention are prepared by any suitable process, including a condensation reaction, such as the well known "Suzuki reaction", as reported by N. Miyaua and A. Suzuki in *Chemical Reviews*, Vol. 95, pp. 457-2483 (1995). This palladium catalyzed reaction can be applied to preparing high molecular weight polymers and copolymers with addition of a phase transfer catalyst as taught in U.S. Pat. No. 5,777,070. The reaction is typically conducted from 70° C. to 120° C. in suitable solvent or diluent. Preferred solvents include aromatic hydrocarbons, such as toluene or diethylbenzene, or aliphatic or aromatic ethers, esters, or carbamates, such as tetrahydrofuran or dimethylformamide. Mixtures of the foregoing solvents or diluents may be employed as well. A most preferred solvent is toluene. An aqueous base, preferably sodium carbonate or bicarbonate, is used as a scavenger for the reaction product of the leaving group, generally HBr. Depending on the reactivities of the reagents and the molecular weight of the desired product, a polymerization reaction may take from 1 minute to 100 hours. A monofunctional aryl halide or an aryl boronate compound may be added as a chain-terminator in such reactions, thereby resulting in the formation of a terminal aryl group.

Polymerization processes involving only dihalo-functional reactants used in the formation of compounds according to the present invention may also be carried out using nickel catalyzed coupling reactions. One such coupling reaction was described by Colon et al. in *Journal of Polymer Science*. Part A, Polymer Chemistry Edition, Vol. 28, p. 367 (1990), incorporated herein by reference, and by Colon et al. in *Journal of Organic Chemistry* Vol. 51, p. 2627 (1986). The reaction is typically conducted in a polar aprotic solvent (e.g., dimethylacetamide) with a catalytic amount of nickel salt, a substantial amount of triphenylphosphine and a large excess of zinc dust. A variant of this process is described by Ioyda et al. in *Bulletin of the Chemical Society of Japan*, Vol. 63, p. 80 (1990) wherein an organo-soluble iodide was used as an accelerator. Another nickel-catalyzed coupling reaction was disclosed by Yamamoto in *Progress in Polymer Science*, Vol. 17, p. 1153 (1992) wherein a mixture of dihaloaromatic compounds were treated with an excess amount of nickel (1,5-cyclooctadiene) complex in an inert solvent. All nickel-catalyzed coupling reactions when applied to reactant mixtures of two or more aromatic dihalides yield essentially random copolymers. Such polymerization reactions may be terminated by the addition of small amounts of water to the polymerization reaction mixture, thereby replacing the terminal halogen groups with hydrogen groups. Alternatively, a monofunctional aryl halide may be used as a chain-terminator, resulting in the formation of a terminal aryl group.

Copolymers Containing Conjugated Groups

The polymers of the invention desirably contain conjugated unsaturated groups along the backbone. "Conjugated groups" refers to moieties containing two or more double bonds, triple bonds and/or aromatic rings, separated by a single covalent bond. The incorporation of such groups into the polymer may be used to modify the light absorption, ionization potential, and/or electronic, properties of the polymer. Preferred unsaturated groups present in the conjugated unsaturated group-containing comonomers for use herein include divalent derivatives of hydrocarbons such as divalent derivatives of benzene, naphthalene, acenaphthene, phenanthrene, anthracene, fluoranthene, pyrene, rubrene, and chrysene, as well as unsaturated heterocyclic groups, such as divalent derivatives of furan, thiophene, pyrrole, oxazole, isooxazole, thiazole, isothiazole, imidazole, oxadiazoles, thiadiazole, pyrazole, pyridine, pyridazine, pyrimidine, pyrazine, triazine, tetrazene; benzoxazole, benzothiazole, benzimidazole, quinoline, isoquinoline, cinnoline, quinazoline, quinoxaline, phthalazine, benzothiadiazole, benzotriazine, phenazine, phenanthridine, acridine, carbazole, and diphenylene oxide. Highly desirable copolymerizable conjugated unsaturated groups include 9,9-disubstituted fluorenediyl groups and triarylamine groups.

It is possible to control the sequencing of the monomeric units in the resulting copolymers by controlling the order and composition of monomer feeds, especially when employing a Suzuki reaction. For instance, a high molecular weight copolymer comprising mainly large blocks of polyfluorenediyl homopolymers connected to short blocks of alternating diarylamine-comonomer oligomers may be made by first introducing into the reaction suitable reactants in the appropriate ratio to make the alternating fluorenediyl-comonomer oligomers followed by the remainder of diarylamine or other monomers so long as there is an overall stoichiometric balance of the reagents, that is, the boron and bromine containing reagents.

Examples of arylamine groups that may be additionally incorporated into the copolymers of the invention are tertiary aromatic amines containing two reactive substituents. Such compounds result in the inclusion of the corresponding triarylamine remnant into the copolymer. Examples of suitable tertiary aromatic amines include, triphenyl amine, alkyldiaryl amines, N,N,N',N'-tetraphenylbenzidine, and N,N,N',N'-tetraphenyl-1,4-phenylenediamine.

In general, copolymerizable, conjugated compounds containing up to 60 carbons are useful for the present purpose. They may be substituted optionally with one or more substituents that are not deleterious to the luminescent properties of the polymer compositions. Examples of suitable substituents include $C_1$-$C_{20}$ hydrocarbyl radicals, $C_1$-$C_{20}$ (thio) alkoxy radicals, $C_1$-$C_{20}$ (thio)aryloxy radicals, cyano, fluoro, chloro, $C_1$-$C_{20}$ alkoxycarbonyl, $C_1$-$C_{20}$ aryoxylcarbonyl, $C_1$-$C_{20}$ carboxyl and alkyl(aryl)sulfonyl radicals. Substituents which are known luminescent quenchers, such as arylcarbonyl and nitro groups, are undesirable and should be avoided.

Polymer Blends

The oligomers and polymers of invention may be used in forming a blend of at least two polymers. If desired, one or more of the oligomers or polymers of the blend may be a light-emitting polymer. Suitably the blend is composed of one or more polymeric materials selected from polystyrene, polybutadiene, poly(methyl methacrylate), poly(ethylene oxide), phenoxy resins, polycarbonates, polyamides, polyesters, polyurethanes, polyimides, crosslinked epoxy resins, crosslinked phenolic resins, crosslinked acrylate resins, and crosslinked urethane resins. Examples of these polymers may be found in *Preparative Methods of Polymer Chemistry* W. R. Sorenson and T. W. Campbell, Second Edition, Interscience Publishers (1968). Preferably the blends comprising a crosslinked polymer are formed by blending the uncrosslinked components and later crosslinking the components in situ.

Preferably the blend comprises at least two conjugated semiconducting polymers and the maximum emission wavelength of one of the polymers in the blend is within 25 nm of the maximum absorption wavelength of at least one other polymer in the blend. Highly desirably the blend comprises a mixture of two polymers each corresponding to the present invention in the range from 0.1 to 99.9 and 99.9 to 0.1 percent respectively.

Polymer Applications

The primary use for the oligomers and polymers of the invention is in the formation of films. Such films can be used in preparing photoluminescent or fluorescent coatings as well as interlayers, protective coating, electron transport, and hole transport layers in electronic devices such as organic light emitting diodes, especially polymeric light-emitting diodes, photovoltaic cells, lighting, photodiodes, sensors, thin film transistors, and other devices. The thickness of the coating or film is dependent upon the ultimate use. Generally, such thickness can be from 0.01 to 200 micrometers. When used as a fluorescent coating, the film thickness is desirably from 50 to 200 micrometers. When used as electronic protective layers, the film thickness is desirably from 5 to 20 micrometers. When used as a layer in a polymeric light-emitting diode, the film thickness is desirably from 0.001 to 2 micrometers. The oligomers or polymers of the invention form films that are substantially lacking in pinholes and other defects. Such films can be prepared by means well known in the art including spin-coating, spray-coating (including ink-jet printing), dip-coating and roller-coating. Such coatings are prepared by a process wherein a composition comprising the present compounds, oligomers or polymers is applied to a substrate and exposed to conditions such that a film is formed, generally by means of a crosslinking reaction. The conditions which form a film depend upon the application technique and the reactive end groups of the film forming moieties. Preferably, the solution contains from 0.1 to 10 weight percent of the oligomers or polymers of the invention, and the remainder solvent. For thin coatings, it is preferred that the composition contains from 0.5 to 5.0 percent by weight of the compounds, oligomers or polymers. This composition is then applied to the appropriate substrate by the desired method and the solvent is allowed to evaporate. Residual solvent may be removed by vacuum and/or by heat. If the solvent is low boiling, then low solution concentrations, for example, 0.1 to 2 percent, are desired. If the solvent is high boiling, then high concentrations, for example, 3 to 10 percent, are desired. After removal of the solvent, the coating is then exposed to the necessary conditions to cure the film, if needed, thereby preparing a film having high solvent and heat resistance. The films are preferably substantially uniform in thickness and substantially free of pinholes. Preferably, the films are cured when exposed to temperatures of 100° C. or greater, more preferably 150° C. or greater and most preferably 200° C. or greater. Preferably, the films cure at a temperature of 300° C. or less.

In the preparation of the films, the composition may further comprise a catalyst suitable to facilitate or initiate the crosslinking process. Such catalysts are well known in the art, for instance, for materials having ethylenic unsaturation, a free radical catalyst may be used. For aryl moieties with glycidyl ethers as end-groups, ureas or imidazoles may be used. In the preparation of films from fluorenes with glycidyl ether substituted aryl groups as terminal moieties, the materials may be reacted with commonly known curing agents which facilitate crosslinking. Among preferred curing agents are tetrahydrophthalic anhydride, methylbicyclo[2.2.1]heptane-2,3-dicarboxylic anhydride (nadic anhydride), and maleic anhydride.

In another desirable embodiment, the monomers and oligomers may be partially cured or B-staged prior to forming the film. In such embodiment, the composition is exposed to conditions such that a portion of the reactive materials cure and a portion of the reactive materials do not cure. This is commonly used to improve the processability of composition and can facilitate the preparation of films. Such B-staged material can thereafter be used to prepare coatings by the means disclosed above. Preferably, from 10 to 50 percent of the reactive moieties are reacted during B-staging.

Yet another aspect of the invention relates to organic electroluminescent (EL) devices comprising a film of the polymers of this invention. An organic EL device typically consists of an organic film located between an anode and a cathode in electrical contact therewith, such that when a positive bias is applied to the device, holes are injected into the organic film from the anode, and electrons are injected into the organic film from the cathode. The subsequent combination of a hole with an electron may give rise to an exciton which may undergo radiative decay to the ground state by liberating a photon. In practice the anode is commonly a mixed oxide of indium and tin (ITO), employed for its high conductivity and transparency. The mixed oxide is normally deposited on a transparent substrate such as glass or plastic so that the light emitted by the organic film may be observed. The organic film may be the composite of several individual layers each designed for a distinct function or purpose. Since holes are injected from the anode, the layer next to the anode desirably has suitable functionality for transporting holes. Similarly, the layer next to the cathode desirably has suitable functionality for transporting electrons. In many instances, the hole or electron transporting layer also acts as the emitting layer. In some instances, one layer performs the combined functions of hole transport, electron transport, and light emission. Generally, films comprising the polymers of the present invention act as buffer layers or hole transport layers in an electronic device. In addition to the foregoing polymeric film layers, films of small molecules deposited by thermal evaporation may be incorporated into the electronic device, if desired. It is preferred that the total thickness of the organic film be less than 1000 nm, more preferably less than 500 nm, most preferably less than 300 nm. One embodiment of the instant invention is an EL device in which the organic film comprises at least one of the polymeric compositions of this invention.

The ITO surface which serves as the anode may be coated with a film according to the invention usually after first cleaning the exposed surface with an aqueous detergent solution, an organic solvent, and/or a UV or plasma generated ozone treatment. It may also be coated with a thin layer of a conducting substance to facilitate hole injection if desired. Suitable conducting substances include copper phthalocyanine, polyamine and poly(3,4-ethylenedioxy-thiophene) (PEDT); the last two of which in their conductive forms are prepared by doping with a strong organic acid, for example, poly (styrenesulfonic acid). It is preferred that the thickness of the conducting layer, when used, be 200 nm or less; more preferably 100 nm or less.

The present compounds may be used in the preparation of interlayers in a multilayer device or as one component of a mixture of compounds forming a hole transporting polymer layer or as a separate hole transporting layer in a multilayer electronic device, especially an electroluminescent device. In the case where a hole-transporting polymer other than the present invention is used, known hole-conducting polymers, such as polyvinylcarbazole, or the polymeric aryl amines disclosed in U.S. Pat. No. 5,728,801 or 5,929,194 may be employed. The resistance of this layer to erosion by the solution of the copolymer film which is to be applied next is obviously critical to the successful fabrication of multi-layer devices. Accordingly the copolymers of this invention are normally applied from solutions in organic solvents such as xylene or toluene in which the hole-transporting layer is insoluble. By covering or protecting the hole-transporting polymer with an interlayer comprising a crosslinked polymer according to the present invention, the hole-transporting polymer can be protected from subsequent reagents or solvents employed in manufacture of the electronic device. The thickness of the hole-transporting layer or interlayer according to the invention is desirably 500 nm or less, preferably 300 nm or less, most preferably 150 nm or less.

A suitable electron-transporting layer, if used, may be applied either by thermal evaporation of a low molecular weight material or by solution coating of a polymer, such as a polymer according to the present invention, using a solvent that does not significantly damage any previously deposited film layer. Examples of low molecular weight materials conventionally used in forming electron-transporting layers include metal complexes of 8-hydroxyquinoline (as described by Burrows et al. in *Applied Physics Letters, Vol.* 64, pp. 2718-2720 (1994)), metallic complexes of 10-hydroxybenzo(h)quinoline (as described by Hamada et al. in *Chemistry Letters, pp.* 906-906 (1993)), 1,3,4-oxadiazoles (as described by Hamada et al. in *Optoelectronics—Devices and Technologies* Vol. 7, pp. 83-93 (1992)), 1,3,4-triazoles (as described by Kido et al. in *Chemistry Letters* pp. 47-48 (1996)), and dicarboximides of perylene (as described by Yoshida et al. in *Applied Physics Letters*, Vol. 69, pp. 734-736 (1996)).

Polymeric electron-transporting materials in addition to those of the present invention are exemplified by 1,3,4-oxadiazole-containing polymers (as described by Li et al. in *Journal of Chemical Society* pp. 2211-2212 (1995), by Yang and Pei in *Journal of Applied Physics* Vol 77, pp. 4807-4809 (1995)), 1,3,4-triazole-containing polymers (as described by Strukelj et al. in *Science, Vol.* 267, pp. 1969-1972 (1995)), quinoxaline-containing polymers (as described by Yamamoto et al. in *Japan Journal of Applied Physics*, Vol. 33, pp. L250-L253 (1994), O'Brien et al. in *Synthetic Metals*, Vol. 76, pp. 105-108 (1996)), and cyano-PPV (as described by Weaver et al. in *Thin Solid Films* Vol. 273, pp. 39-47 (1996)). The thickness of this layer may be 500 nm or less, preferably 300 nm or less, most preferably 150 nm or less.

The final layer in the electronic device is normally the cathode, which may be formed from any conductive material, preferably a metal. Examples of suitable metals include lithium, calcium, magnesium, indium, silver, aluminum, or blends and alloys of the above. A metallic cathode may be deposited either by thermal evaporation or by sputtering, according to known techniques. The thickness of the cathode may be from 100 nm to 10,000 nm. The preferred metals are calcium, magnesium, indium, and aluminum. Alloys of these metals may also be used. Alloys of aluminum containing 1 to 5 percent of lithium and alloys of magnesium containing at least 80 percent magnesium are highly preferred.

The EL devices of this invention emit light when subjected to an applied voltage of 50 volts or less. If desired, an encapsulating or protecting coating may be applied to one or more exposed surfaces of the finished device.

In a preferred embodiment, the electroluminescent device comprises at least one hole-transporting polymer film and a light-emitting polymer film at least one of which is comprised of a polymer of the invention, arranged between an anode material and a cathode material such that under an applied voltage, holes are injected from the anode material into the hole-transporting polymer film and electrons are injected from the cathode material into the light-emitting polymer films when the device is forward biased, resulting in light emission from the light-emitting layer. In another preferred embodiment, layers of hole-transporting polymers are arranged so that the layer closest to the anode has the lower oxidation potential, with the adjacent layers having progressively higher oxidation potentials. By these methods, electroluminescent devices having relatively high light output per unit voltage may be prepared.

The term "hole-transporting polymer film" as used herein refers to a layer of a film of a polymer which when disposed between two electrodes to which a field is applied and holes are injected from the anode, permits adequate transport of holes into the emitting polymer. The term "light-emitting polymer film" as used herein refers to a layer of a film of a polymer whose excited states can relax to the ground state by emitting photons, preferably corresponding to wavelengths in the visible light range. The term "anode material" as used herein refers to a semi-transparent, or transparent, conducting film with a work function between 4.5 electron volts (eV) and 5.5 eV. Examples are gold and oxides and mixed oxides of indium and tin. The term "cathode material" as used herein refers to a conducting film desirably having a work function between 2.5 eV and 4.5 eV.

The monomers of the invention possess significant commercial advantages due to the chemical properties attributable thereto. In particular, the following significant benefits may be enumerated.

1. Control of solubility of the material—Polymers according to the invention can be processed from a variety of standard solvents into thin films. After the film is heated, causing the cure reaction to occur, the polymers possess reduced solubility and may become completely insoluble if enough of the curable monomer is present. This allows the manufacturer to prepare multilayered devices from common solvents. Without the ability to cure the film, applying a second layer would dissolve or erode the previous layer.

2. Increased glass transition temperature—Linear semiconducting polymers are thermoplastic and exhibit a glass transition temperature at which the material softens. In electronic devices, especially during fabrication, it is sometimes advantageous to have a high Tg, or no Tg at all. Thermal analysis of the present b-staged polymers shows a Tg before cure and an increase or disappearance of the Tg after the cure reaction. The amount of change to the Tg is controlled by the amount of the functional monomer in the polymer. Highly crosslinked (higher levels of functional monomers) polymers show no Tg.

3. Thermal dimensional stability—Because the cured polymers are cross-linked, they do not soften on heating (Tg) and therefore possess improved dimensional stability. Polymers having a low coefficient of thermal expansion are advantageously employed in thin film/electronic devices.

4. Improved performance in electronic devices—Fabrication of polymer light emitting diodes employing the curable monomers of the present invention, especially by use of higher film drying temperatures achieves significantly improved efficiency and lifetime.

5. Improved thin film properties—By advancing the polymers molecular weight through the cure reaction, the strength and hardness of thin films are increased compared to the use of a lower molecular weight pre-cured material. These are important properties for most thin film applications, including use in electronic devices.

6. Advanceable molecular weights—The molecular weight of the present polymers can be increased from that of the pre-cured precursor by heating the material above the cure activation temperature either in solvent or neat or solid form. These groups can also be reacted with other groups that can be added to the polymer, resulting in the ability to provide multiple molecular weight products through controlling the degree of curing.

7. Control of crystallinity and morphology—The presence of curable functionality in the polymers of the invention allows for the preparation of a branched polymer network or a highly crosslinked network depending on the quantity of cross-linking functionality present. Because semiconducting, polyconjugated polymers tend to be semicrystalline, orientation of polymer chains, leading to crystal formation can occur. Introducing branch points through cross-linking functionality disrupts the tendency of the uncured polymers to crystallize or orient.

8. Increased Polymer Lifetime—Crosslinking "freezes" the morphology of the polymer by tying the polymer chains together. Controlling the morphology of the polymeric film and insuring that it doesn't change with time are advantageous properties for polymers used in thin film electronic applications.

It is expressly intended that the foregoing disclosure of preferred or desired, more preferred or more desired, highly preferred or highly desired, or most preferred or most desired substituents, ranges, end uses, processes, or combinations with respect to any one of the embodiments of the invention is applicable as well to any other of the preceding or succeeding embodiments of the invention, independently of the identity of any other specific substituent, range, use, process, or combination.

The following examples are included for illustrative purposes only and are not intended to limit the scope of the claims. Unless otherwise stated, implicit from the context or conventional in the art, all parts and percentages herein are based on weight. It is understood that the present invention is operable in the absence of any component which has not been specifically disclosed. The term "overnight", if used, refers to a time of approximately 16-18 hours and "room temperature", if used, refers to a temperature of about 20-25° C.

EXAMPLE 1

Typical Suzuki coupling reaction conditions are used to prepare a cross-linked polymer from the following 6 monomer units. The quantities of respective monomer units employed are disclosed in Table 1. The resulting polymer composition is disclosed in Table 2.

Monomers

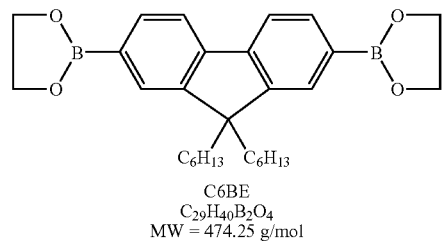

C6BE
$C_{29}H_{40}B_2O_4$
MW = 474.25 g/mol

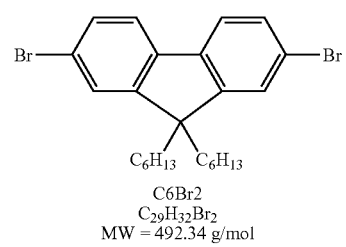

C6Br2
$C_{29}H_{32}Br_2$
MW = 492.34 g/mol

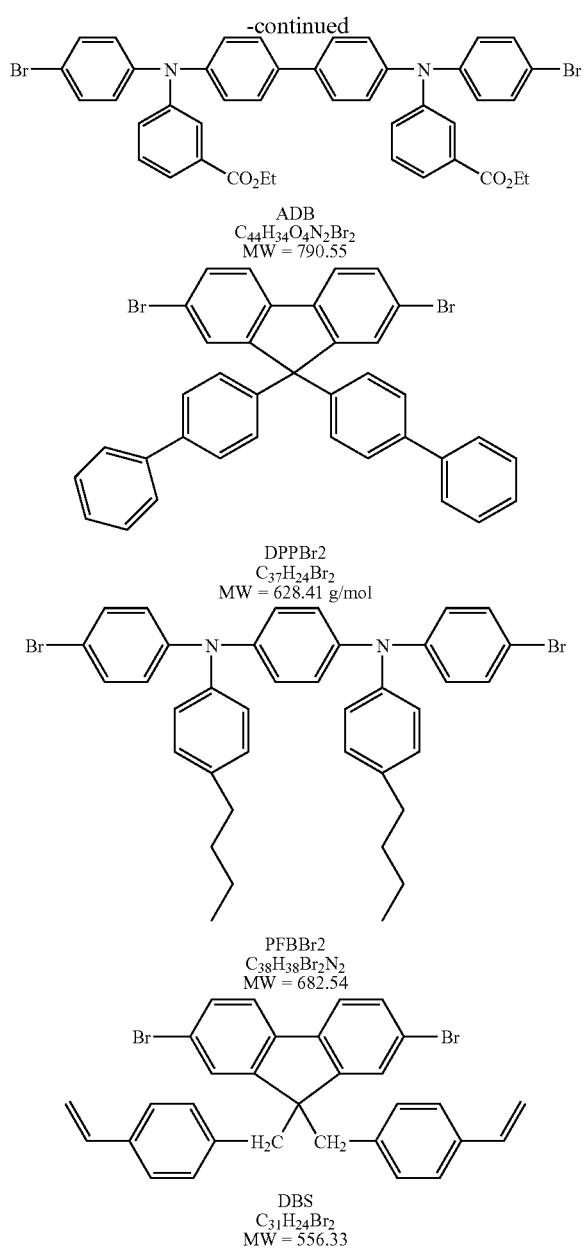

Monomer Synthesis

1) C6BE (2,7-Bis(1,3,2-dioxaborolan-2-yl)-9,9-dioctylfluorene)

A 500 mL, three-necked, round bottom flask, equipped with an overhead stirrer, an addition funnel and a condenser which is connected to a nitrogen line, is charged with 2,7-dibromo-9,9-dioctylfluorene (21.9 g, 40 mmol) and TBF (200 mL). The mixture is stirred and cooled in an acetone-dry ice bath to about −77° C. With nitrogen on, n-butyllithium (2.5 M in hexane, 33.6 mL, 84 mmol) is added dropwise in about 10 min. A yellow solution is formed which turned to cloudy gradually. The mixture is stirred at −77° C. for another 90 min. Tri-isopropylborate (22.6 g, 120 mmol) is then added dropwise over 15 min, during the time the mixture turned into a thick white gel-like material. The cooling bath is removed, and the mixture is warmed up to ambient temperature. The reaction is vigorously stirred for another 2 hours. The mixture is slowly poured into a beaker with 500 g of crushed ice and 100 mL of concentrated hydrochloric acid, then transferred to a separatory funnel and extracted with toluene (3×200 mL). The extracts are combined, washed with saturated brine (2×100 mL), and the volume is reduced to about 250 mL by rotary evaporation. HPLC analysis indicates the sample contains >90% of diboronic acid intermediate.

To the above solution in a 500 mL, three-necked, round bottom flask, equipped with a magnetic stirrer and a Dean-Stark trap connected with a condenser, is added ethylene glycol (7.5 g, 120 mmol). The mixture is stirred and refluxed under nitrogen for 6 hours and about 25 mL of toluene-water azeotrope is drained off. The solvent is removed by rotary evaporation, and the residual oil is crystallized from hexane on cooling in a refrigerator. The product obtained is a white crystalline powdered material, 17.5 g (82.5 percent). HPLC analysis indicates the product is in >99% purity. $^1$H and $^{13}$C-NMR spectra are consistent with the structure of the expected product.

2) C6Br2 (2,7-dibromo-9,9-dihexylfluorene)

An 1 liter, three-necked, round bottom flask, equipped with an overhead stirrer, an addition funnel and a condenser which is connected to a nitrogen line, is charged with 2,7-dibromofluorene (65.2 g, 0.20 mol), aqueous sodium hydroxide (50 percent, 80 mL, 1.00 mol), benzyltriethylammonium chloride (4.0 g, 17.56 mmol) and DMSO (235 mL). With a slow purge of nitrogen through the condenser, n-hexyl bromide (87.4 g, 0.53 mol) is added dropwise with vigorous stirring. The temperature of the reaction rises to about 85° C. within 15 min and the color of the reaction changes to blue. The reaction is allowed to stir for 2 hour until the temperature decreases to ambient temperature. The blue heterogenous material is gradually added to a beaker with ice/water (~600 mL) and concentrated hydrochloric acid (101 ml). The resultant mixture is stirred for 30 min and the precipitate is filtered, washed with water and dried in air. The crude product is then mechanically stirred in acetonitrile (800 mL) for 12 hours. The product is collected by filtration, washed with acetonitrile, and dried in a vacuum oven at 40° C. for 12 hours to give 93.5 g (95 percent) of an off-white powdered material. HPLC analysis indicates the product is in >98 percent purity.

For further purification, the above crude product (50 g) is dissolved in toluene (200 mL), passed through a column packed with Celite™ brand filter aid (7×1 cm), silica gel (7×15 cm) and Celite™ (7×1 cm) eluted with toluene. The solvent as removed by rotary evaporation and the residual thick oil is crystallized from toluene-ethanol. The product is collected by filtration, washed with ethanol and dried in a vacuum oven at 40° C. for 16 hours to give 46 g (92 percent) of light-yellow needles. $^1$H- and $^{13}$C-NMR spectra are consistent with the structure of the expected product.

3) ADB (N,N'-Di(4-Bromophenyl)-N,N'-di(3-ethoxycarbonylphenyl)-benzidine)

A 1 liter, three-necked, round-bottomed flask, equipped with an overhead stirrer, a Dean-Stark receiver, which is adopted with a reflux condenser and a nitrogen line, is charged with N,N'-diphenylbenzidine (60.0 g, 178 mmol), ethyl 3-iodobenzoate (123 g, 445 mmol), copper bronze powder (27 g, 502 mmol), powdered potassium carbonate (66 g. 478 mmol) and 1,2-dichlorobenzene (390 mL). With a slow purge of nitrogen through the condenser, the reaction vessel is placed in a heating mantle and the stirred reaction is stirred and gently refluxed at 220° C. for 16 hours. About 25 mL of water-dichlorobenzene is collected during time. HPLC analysis indicates 99 percent product formation. After cooling, the mixture is filtered through a layer of Celite™ to remove the solid materials. The celite is washed with toluene. The filtrates are combined and the major part of the solvent is removed by rotary evaporation. The solvent residue is further removed with a Krugerlrohr apparatus to afford a brown viscous oil. Flush chromatography on an alumina column (basic) and removal of the solvent affords a thick oil, which, on standing, solidifies at ambient temperature. Crystallization from toluene-ethanol provides 97.8 g (87 percent) of product, N,N'-di(ethyl 3-phenylcarboxylate)-benzidine, as a light yellow powdered material.

To a 1000 mL, three-necked round bottle flask, equipped with a mechanical stirrer, an addition funnel and a nitrogen line, are added N,N'-di(ethyl 3-phenylcarboxylate)-benzidine (40 g, 63 mmol) and dimethylformamide (DMF) (250 mL). To the stirring mixture is added dropwise a solution of N-bromosuccinimide (23 g, 129 mmol) in DMF (70 mL) over 20 min. The mixture is stirred at ambient temperature for 3 hours. During the time the product precipitates from the solution. To the mixture is then added ethanol (150 mL) and stirring is continued for 1 hour. The solid is collected by filtration, washed with ethanol and dried in air. The crude product is redissolved in toluene, passed through a short silica gel column eluted with toluene. The solvent is removed by rotary evaporation, and the residual solid is recrystallized from toluene-ethanol. The product is collected by filtration, washed with ethanol and dried in a vacuum oven at 65° C. for 8 hours to give 33.6 g (68 percent) of white needles. HPLC analysis indicates the product is >98 percent in purity. $^1$H and $^{13}$C-NMR spectra are consistent with the structure of the expected product.

4) PPPBr2 (2,7-dibromo-9,9-dibiphenylfluorene)

A 1 L, three-necked, round bottom flask, equipped with an overhead stirrer and a reflux condenser which is connected to a nitrogen line is charged with 4-Bromobiphenyl (23.3 g, 100 mmol) and hexane (250 mL). To the stirring mixture, n-BuLi (41 mL, 102 mmol, 2.5 M in hexane) is added dropwise with a syringe through a septum. The resulting mixture is then stirred and heated to gentle refluxing for 1 hour. The mixture is cooled to −70° C. in an isopropanol/dry ice bath, and during this procedure the lithium salt precipitates. The resulting suspension is diluted dropwise with dry THF (100 mL). And a solution of 4,4-dibromobiphenyl-2-Carboxylate (17.8 g, 50 mmol) in 50 mL of dry THF is added dropwise. The mixture is stirred at −70° C. for 30 minutes and is then allowed to warm to ambient temperature and to stir for another 3 hours. The reaction is quenched with water (40 mL) and then acidified with diluted hydrochloric acid. The mixture is extracted with ether (3×100 mL) and the combined ether solution is washed with saturated brine, dried with MgSO$_4$, filtered and concentrated to give a thick oil.

In a 500 mL, three-necked, round bottom flask, equipped with an overhead stirrer and a reflux condenser connected to a nitrogen line and containing the oil, acetic acid (100 mL) is added. Concentrated sulfuric acid (5 mL) is slowly added and the mixture is stirred and heated at 125° C. for 3 hours. After cooling, ethanol (50 mL) is added and the mixture is stirred for 30 minutes. The resulting precipitate is collected by filtration, washed with ethanol, and dried in air.

The crude product is dissolved in methylene chloride (150 mL), washed with sodium carbonate (100 mL, 0.2 M) and dried with MgSO$_4$. The solution is passed through a silica gel column (4.5×15 cm) and eluted with methylene chloride. The product containing fractions are collected and the solvent removed. The residual solid is recrystallized from CH$_2$Cl$_2$/CH$_3$CN to give 24.8 g (79 percent) of a white crystalline product. The purity by HPLC is nearly 100 percent and $^1$H- and $^{13}$C-NMR spectra are consistent with the structure of DPPBr2.

5) PFBBr2 (N,N'-Diphenyl-N,N'-di-(4-n-butylphenyl)-1,4-phenylenediamine)

A 1000 mL, three-necked, round bottom flask, equipped with an overhead stirrer and a reflex condenser which is connected to a nitrogen line, is charged with palladium acetate (405 mg, 1.8 mmol), tri-o-tolylphosphine (1.21 g, 3.9 mmol), and toluene (30 mL). The mixture is stirred at ambient temperature for 10 minutes until a homogenous yellow solution forms. To this solution are added N,N'-diphenyl-1,4-phenylenediamine (11.7 g, 45 mmol), 4-n-butylbromobenzene (21.3 g, 100 mmol), sodium tert-butoxide (9.61 g, 100 mmol), and more toluene (370 mL). With a slow purge of nitrogen through the condenser, the reaction vessel is placed into an oil-bath and the stirred reaction is heated to reflux for 12 hours. To the cooled mixture concentrated hydrochloric acid (38 percent, 11 mL) is added, and the stirring is continued for one hour. The solution is passed through a short column (neutral alumina, 6.5×11 cm) and eluted with toluene. The major part of the solvent is evaporated and the residual solvent is further removed with a Krugerlrohr apparatus to afford a light brown viscous oil. Crystallization from acetone/methanol affords 15.9 g (67 percent) of product as white flacks. HPLC analysis indicates the product is in >98 percent purity. $^1$H and $^{13}$C NMR spectra are consistent with the product, N,N'-diphenyl-N,N'-di-(4-n-butylphenyl)-1,4-phenylenediamine.

To a 500 mL, three-necked, round bottle flask equipped with a mechanical stirrer, condenser which is attached to a nitrogen line is added N,N'-diphenyl-N,N'-di-(4-n-butylphenyl)-1,4-phenylenediamine (10.50 g, 20.0 mmol), DMF (80 mL) and THF (80 mL). To the stirring mixture is added a solution of N-bromosuccinimide (7.92 g, 44.0 mmol) in 20 mL of DMF over 10 minutes. The resultant mixture is then stirred at ambient temperature for 3 hours. The volume of the solvent is reduced to about 50 mL on a rotary evaporator. Ethanol (150 mL) is added and the mixture stirred at ambient temperature for one hour. The crude product is collected by filtration, washed with ethanol and dried in air. The product is redissolved in toluene (100 mL) and the solution is flush chromatographed through a neutral alumina column (6.5×10 cm) eluted with toluene. The solvent is removed by rotary evaporation and the residue is recrystallized from acetone-ethanol. The product is collected by filtration, washed with ethanol and dried in a vacuum oven at 65° C. for 8 hours to give 13.7 g (86 percent) of white needles. HPLC analysis indicates the product is nearly 100 percent in purity. $^1$H and $^{13}$C NMR spectra are consistent with the structure of PFBBr2.

6) DBS (2,7-dibromo-9,9-di(vinylbenzyl)fluorene)

Under a nitrogen atmosphere 2,7-dibromofluorene (6.5 g, 20 mmol) and 4-vinylbenzylchloride (6.72 g, 44 mmol) are placed in a 500 mL round bottom, three necked flask. 100 mL of dimethylsulfoxide (DMSO) is added along with 1.00 g of benzyltriethylammonium chloride phase transfer catalyst. Stirring is commenced and 20 mL of 50 percent aqueous NaOH is added. Additional DMSO (40 mL) is added and the solution is heated to 60° C. for 2 hours. The solution is poured over ice and 250 mL of 1N aqueous HCl is added. After stirring for 1 hour, the solid is recovered and rinsed with water and dried. The product is dissolved in methanol, filtered, rinsed with methanol and water and dried in a vacuum oven at 55° C. overnight.

TABLE 1

| monomer | Purity (percent) | MW | mmol | Grams used |
|---------|------------------|--------|--------|------------|
| C6BE    | 99.9             | 474.26 | 6.8110 | 3.2339     |
| C6Br2   | 99.8             | 492.34 | 4.9431 | 2.4384     |
| ADB     | 99.5             | 790.55 | 0.6937 | 0.5512     |
| DPPBr2  | 99.0             | 628.41 | 0.3469 | 0.2179     |
| PFBBr2  | 99.0             | 682.54 | 0.6937 | 0.4782     |
| DBS     | 100.0            | 556.33 | 0.3469 | 0.1930     |

TABLE 2

| Polymer unit | MW     | Mol Ratio | Weight Percent |
|--------------|--------|-----------|----------------|
| C6-C6        | 665.06 | 0.70      | 64.2           |
| C6-ADB       | 963.27 | 0.10      | 13.4           |
| C6-DPP       | 801.13 | 0.05      | 5.6            |
| C6-PFBB      | 855.26 | 0.10      | 11.9           |
| C6-DBS       | 825.59 | 0.05      | 5.8            |

The listed reactants along with tetrakis(triphenylphosphine)palladium catalyst (7.5 mg, 65.8 mmol), $Na_2CO_3$ (15 ml of 2M aqueous solution), tricaprylmethylammonium chloride surfactant (0.97 g) and 35 mL of toluene are loaded into a 250 mL, 3-neck, round bottom flask equipped with a nitrogen line, overhead stirring, a condenser, and an oil bath for heating. The mixture is heated in a 95° C. oil bath for about 19 hrs. The viscosity of the organic phase slowly increased over the course of the reaction. A light yellow slightly viscous toluene solution results. The molecular weight as measured by scanning electron calorimetry (SEC) is 80K. The product is end capped by addition of 0.1 g of bromobenzene and 0.15 g of phenylboronic acid and reheating to 95° C. for 4-6 hrs.

After cooling, the aqueous layer is removed, the organic layer is washed with water and the mixture placed back into the flask and heated to 80° C. with diethyldithiocarbamic acid sodium salt trihydrate and allowed to stir overnight. After cooling, the aqueous layer is removed and the organic layer washed twice with a 2 percent aqueous solution of acetic acid (2×300 mL). The remaining organic solution is passed through a column packed with diatomaceous earth filter aid, silica gel, basic alumina, and a second layer of diatomaceous earth, using toluene as the eluent. The collected solution is concentrated by rotary evaporation and precipitated from methanol. The polymer is collected by suction filtration, air dried, and then placed in a vacuum oven at 50° C. overnight to dry. The dried polymer is re-dissolved in toluene, precipitated from methanol, filtered, and placed in a vacuum over at 50° C. to dry. The molecular weight of the isolated polymer as determined by SEC is 94K.

A cured, cross-linked composition is prepared by heating a small sample in a differential scanning calorimeter. Under first heating, the inflection point is located at 132° C. with exotherm peaks at 158° C. and 214° C. A second heating scan shows only a single inflection located at 117° C., thereby indicating that the sample is fully cross-linked.

EXAMPLE 2

The following reaction scheme discloses the preparation of a triarylaminedibromide compound containing a crosslinkable benzocyclobutane functional group and its use in a polymerization reaction with 9,9-di(vinylbenzyl)-2,7-fluorenyl diboronate and di(p-bromophenyl)(p-i-butylphenyl)amine to make a crosslinkable copolymer according to the invention.

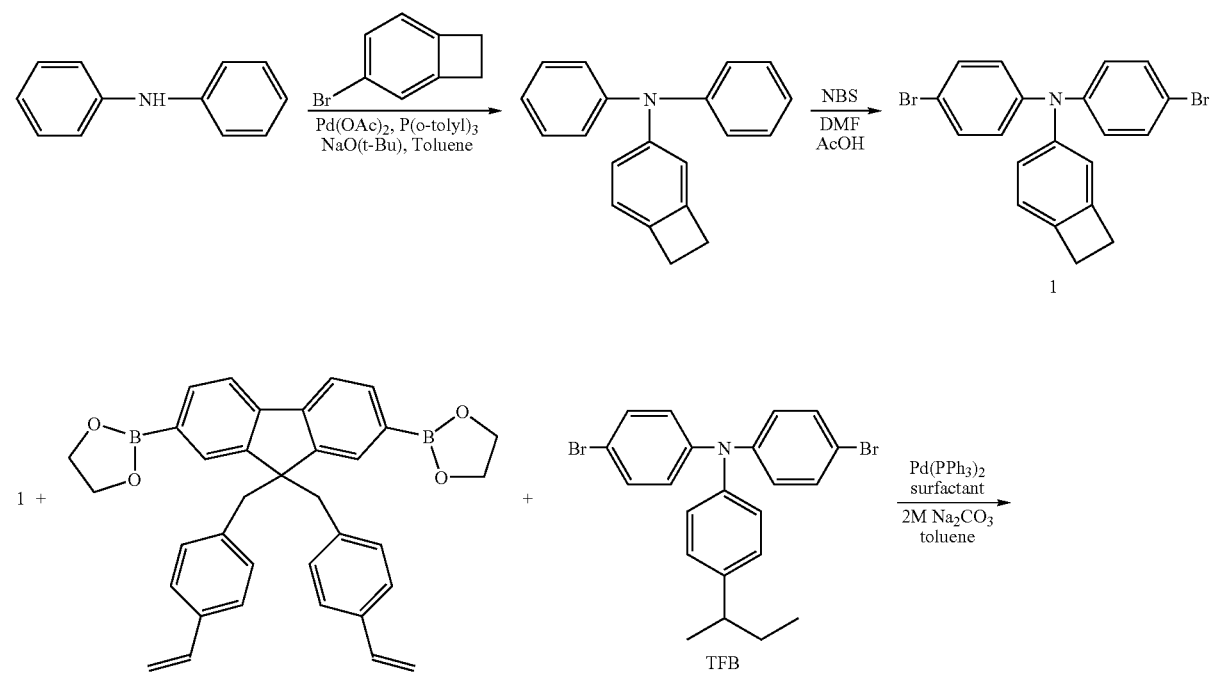

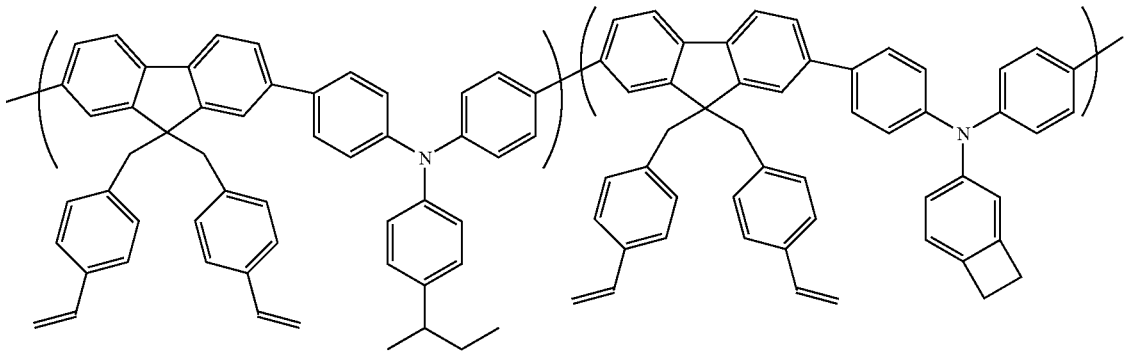

A) Synthesis of diphenylbenzocyclobutaneamine

To a 500 ml, 3-neck round bottom flask equipped with a mechanical stirrer, nitrogen inlet, and reflux condenser (with nitrogen outlet), palladium (I) acetate (196 mg, 1.20 mmol) and tri(o-tolyl)phosphine (731 mg, 2.40 mmol) are added to 100 ml toluene. The mixture is stirred at room temperature under nitrogen until the palladium catalyst dissolves and the solution turns yellow. Diphenyl amine (20.0 g, 118 mmol), bromo benzocyclobutane (23.8 g, 130 mmol) and 400 ml toluene are added, followed by sodium t-butoxide (22.8 g, 237 mmol). Upon addition of the sodium t-butoxide the reaction turns black. The reaction is heated to reflux under nitrogen for 22 hours. The reaction is quenched by addition of 30 ml of aqueous 1 M HCl. The toluene layer is washed with 2M $Na_2CO_3$ (100 ml) then the toluene solution is passed through basic alumina. Evaporation of the toluene gives a yellow oil. The product is precipitated by stirring the oil with isopropanol. The solids are collected and recrystallized from hot isopropanol. $^1$H NMR ($CDCl_3$-d) δ: 7.3-6.8 (m, 13H, Ar), 3.12 (d, 4K, —$CH_2CH_2$—).

B) Synthesis of di(4-Bromophenyl)benzocyclobutane amine (1)

To a 250 ml round bottom flask, diphenylbenzocyclobutaneamine (8.00 g, 29.5 mmol) is added to 100 ml dimethylformamide (DMF) containing 5 drops of glacial acetic acid. To the stirring solution, N-bromosuccinimide (NBS, 10.5 g, 60.7 mmol, 1.97 eq.) is added. After stirring for 5 hours, the reaction is quenched by pouring the reaction mixture into 600 ml of methanol/water (1:1 by vol). A gray solid is recovered by filtration and recrystallized from isopropanol. $^1$H NMR ($CDCl_3$-d) δ: 7.3 (d, 4H, Ar), 7.0 (d, 4H, Ar), 6.95 (t, Ar), 6.8 (s, Ar), 3.12 (d, 4H, —$CH_2CH_2$—).

C) Synthesis of 2,7-Bis(1,3,2-dioxyborole)-9,9-di(p-vinylbenzyl)fluorene

This monomer is synthesized by reaction of tri-isopropylborate with 2,7-dibromo-9,9-di(p-vinylbenzyl)fluorene (DBS) substantially according to the technique of monomer synthesis 1).

D) Synthesis of Polymer

The polymer forming conditions of Example 1 are substantially repeated to form a polymer according to the invention.

The invention claimed is:

1. A crosslinkable oligomer or polymer of the formula:

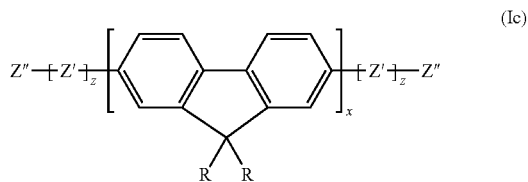

where R, independently each occurrence, is an inert substituent, a monovalent crosslink forming group, X, or a polyvalent crosslink forming group, X', with the proviso that in at least one repeat unit per molecule, at least one R is X or X';

x is a number from 1 to 10,000 and z is a number from 1 to 10,000 signifying the average number of repeat units in the composition;

Z" is a monovalent chain terminating group; and

Z' is independently each occurrence selected from the group consisting of monomers of the formula:

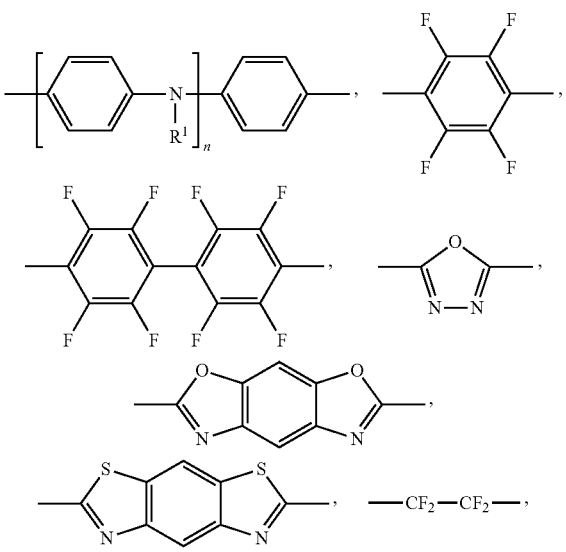

-continued

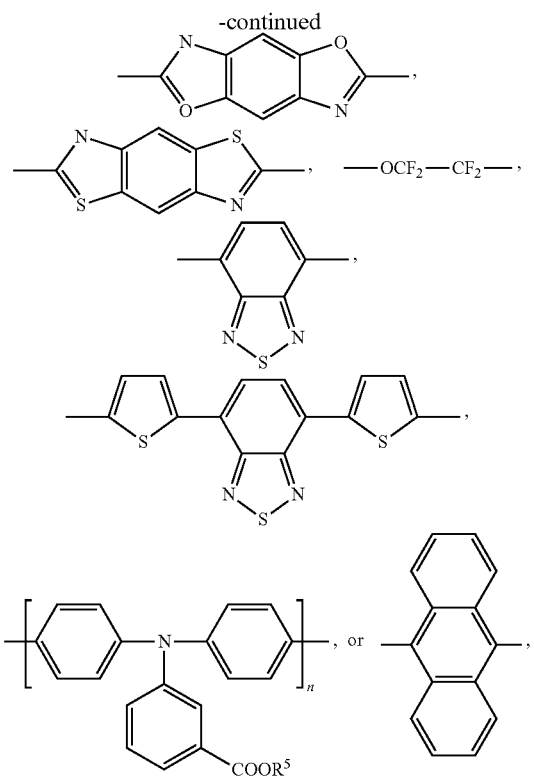

where R[1], independently each occurrence, is an inert substituent, X or X', R[5] is $C_{1-10}$ alkyl, aryl or aralkyl; and n is 1 or 2.

2. The crosslinkable oligomer or polymer according to claim 1 having the structure:

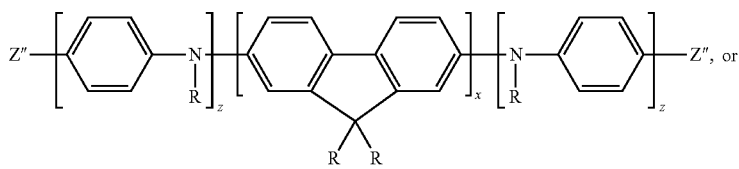

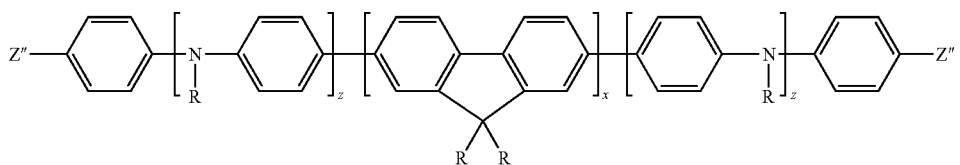

where R, independently each occurrence, is an inert substituent, a monovalent crosslink forming group, X, or a polyvalent crosslink forming group, X', with the proviso that in at least one repeat unit per molecule, at least one R is X or X';

x is a number from 1 to 10,000 and z is a number from 1 to 10,000 signifying the average number of repeat units in the composition;

and Z" is a monovalent chain terminating group.

3. A cross-linked polymer corresponding to formula:

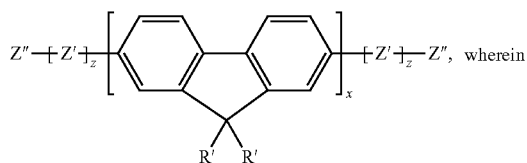

R' independently each occurrence is R or a crosslinked derivative of X or X' with the proviso, that in at least one occurrence, R' is a crosslinked derivative of X or X', X is a monovalent crosslink forming group, X' is a polyvalent crosslink forming group, R is an inert substituent, x is a number from 1 to 10,000, Z" is a monovalent chain terminating group; Z' is independently each occurrence selected from the group consisting of monomers of the formula:

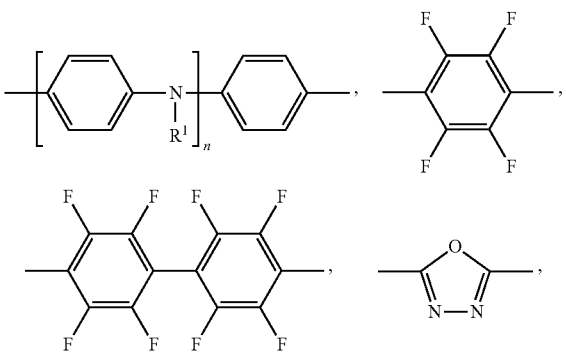

-continued

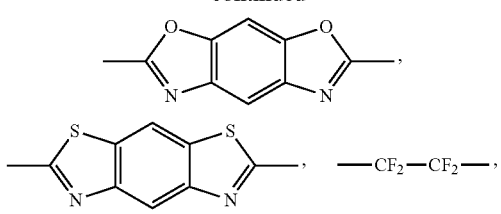

-continued

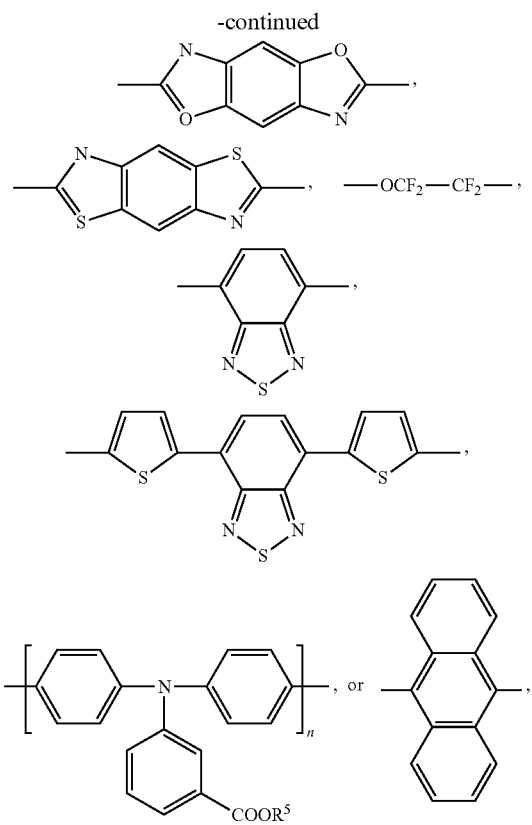

and z is a number from 1 to 10,000 signifying the average number of repeating units in the composition, where $R^1$, independently each occurrence, is an inert substituent, X or X', $R^5$ is $C_{1-10}$ alkyl, aryl or aralkyl; and n is 1 or 2.

4. A process for preparing oligomers or polymers of claim 1, which process comprises heating one or more compounds containing one or more fluorendiyl groups of the formula:

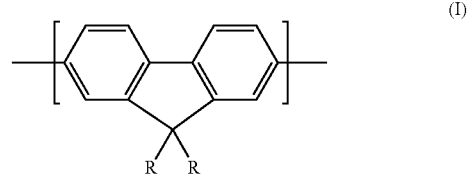

where R, independently each occurrence, is an inert substituent, a monovalent crosslink forming group, X, or a polyvalent crosslink forming group, X', with the provisio that in at least one repeat unit per molecule, at least one R is X or X' or a composition comprising the same, optionally in the presence of a noninterfering compound, under reaction conditions sufficient to form an oligomer or polymer of claim 1.

5. A film comprising one or more of the oligomers or polymers according to claim 1.

6. An electronic device comprising one or more layers of polymer films, at least one of which comprises a film according to claim 5.

7. A film comprising one or more of the oligomers or polymers according to claim 2.

8. A film comprising one or more of the oligomers or polymers according to claim 3.

9. A film prepared according to claim 4.

* * * * *